(12) United States Patent
Vadgama et al.

(10) Patent No.: US 6,200,772 B1
(45) Date of Patent: Mar. 13, 2001

(54) MODIFIED POLYURETHANE MEMBRANE SENSORS AND ANALYTICAL METHODS

(75) Inventors: Pankaj Maganlal Vadgama, Manchester; Geraldine Patricia Rigby, Merseyside; Sayed Ahmed, Blackburn, all of (GB)

(73) Assignee: Sensalyse Holdings Limited, Manchester (GB)

( * ) Notice: Subject to any disclaimer, the term of this patent is extended or adjusted under 35 U.S.C. 154(b) by 0 days.

(21) Appl. No.: 09/486,180

(22) PCT Filed: Aug. 17, 1998

(86) PCT No.: PCT/GB98/02457

§ 371 Date: May 10, 2000

§ 102(e) Date: May 10, 2000

(87) PCT Pub. No.: WO99/10520

PCT Pub. Date: Mar. 4, 1999

(30) Foreign Application Priority Data

Aug. 23, 1997 (GB) .................................... 9717906

(51) Int. Cl.$^7$ .................................. C12Q 1/26; C12Q 1/00
(52) U.S. Cl. .................................... 435/25; 435/4
(58) Field of Search ................ 435/25, 4, 283.1

(56) References Cited

U.S. PATENT DOCUMENTS

| 3,826,768 | 7/1974 | Suzuki et al. | 260/29.2 |
| 5,707,502 | 1/1998 | McCaffrey et al. | 204/403 |
| 5,759,364 | 6/1998 | Charlton et al. | 204/403 |

FOREIGN PATENT DOCUMENTS

| 38 31 503 | 3/1990 | (DE) . |
| 0 467 219 | 1/1992 | (EP) . |
| 0 535 898 | 4/1993 | (EP) . |
| 0 690 134 | 1/1996 | (EP) . |
| WO 94/25622 | 11/1994 | (WO) . |
| 9828614 A1 * | 7/1998 | (WO) . |
| 9910520 A1 * | 3/1999 | (WO) . |

* cited by examiner

Primary Examiner—Louis N. Leary
(74) Attorney, Agent, or Firm—Pillsbury Madison & Sutro LLP

(57) ABSTRACT

Sensor devices, and analytical methods using them, employing a detector protected from direct contact with samples being examined by a membrane made of a polyurethane modified with a non-ionic surfactant. The detector is preferably an electrode of conventional type (e.g. plantinum metal, optionally with pseudo, counter or reference electrodes) but especially an enzyme electrode. The surfactant may be incorporated into the polyurethane by admixture or by reacting chemically with the polyurethane, and is preferably a condensate of ethylene oxide with a compound containing a hydrophobic moiety—especially with a hydroxy-compound, e.g. an alkylated phenol, fatty alcohol or a sorbitan ester. Conveniently, the polyurethane membrane may contain up to 20 parts per 100 of polyurethane and be up to 10 microns thick, and formed by dip-coating an electrode. Measurements, using electrodes, may be made amperometrically.

22 Claims, 1 Drawing Sheet

MODIFIED POLYURETHANE MEMBRANE SENSORS AND ANALYTICAL METHODS

Figure 1:
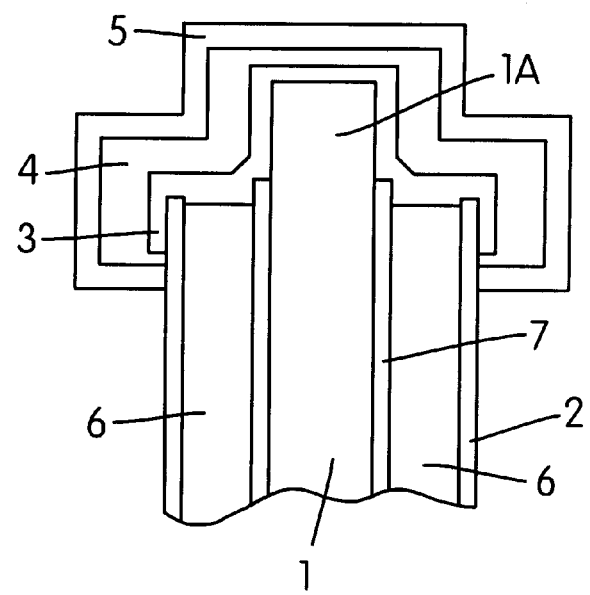

This application is the national phase of international application PCT/GB98/02457 filed Aug. 17, 1998 which designated the U.S.

This invention relates to sensor devices, and more particularly to improved sensor devices useful in analytical methods involving the detection or measurement of analytes, especially in enzyme-based sensor systems.

It is well known to make a variety of sensor devices in which an electrode is employed to provide output signals by which the presence or absence of an analyte in a sample can be determined. For this, an analyte (or a species derived from it) which is electro-active generates a detectable signal at an electrode, and this signal can be used as the basis for detection or measurement of the presence and/or amount of the analyte in a sample.

Bio-sensors have been found to be very successful in use for such purposes, especially when the bio-component is an enzyme. An enzyme has the advantage that it can be more specific to the analyte sought and also, when the analyte itself is not sufficiently electro-active, can be used to interact with the analyte to generate another species which is electro-active and to which the electrode can respond to produce the desired output signals. The classic example of such a sensor is the glucose oxidase enzyme-electrode, in which an immobilised glucose oxidase enzyme catalyses the oxidation of glucose to form hydrogen peroxide, which is then detected and determined by amperometric measurement of the effect it produces (increase in electrical current) at a polarised electrode.

Many such sensors have been proposed, and most of these rely upon some form of membrane to control the extent to which the analyte (e.g. glucose) present in a sample under investigation can gain access to the sensing electrode, at which it can the be detected and determined. The main function of the membrane is to separate as far as possible those components which are desirable from interferents, i.e. components which interfere with the desired determination reactions or take part in reactions of their own which compete with those of the analyte compound sought and distort or overwhelm the signals to be measured.

Many different materials have been proposed for use in such membranes—some as the material forming the membrane itself, and some as coatings to be carried on the surface of another material. In general, these may function either by their porosity (whereby the selectivity of the membrane will depend on which individual components can pass through the pores or holes) or by their permeability (whereby the selectivity of the membrane will depend on which individual components can pass through the membrane material itself).

It is difficult to find membranes which are sufficiently satisfactory or reliable in use, and especially in vivo.

We have now found that, although polyurethanes are among the various materials hitherto proposed for membranes, an unexpectedly satisfactory form of sensor is obtained when the membrane is made of a polyurethane modified with a non-ionic surfactant.

Thus according to our invention we provide an improved sensor device which comprises a detector means and a membrane positioned to protect the detector from direct contact with a sample to be examined, characterised in that the said membrane comprises a modified polyurethane which is substantially non-porous and incorporates a non-ionic surfactant as modifier.

Especially, we provide an improved sensor device which comprises an active (working) electrode and a membrane positioned to protect the electrode from direct contact with a sample to be examined, characterised in that the said membrane comprises a modified polyurethane which is substantially non-porous and incorporates a non-ionic surfactant as modifier.

According to our invention we also provide the modified polyurethanes, wherein the modifier incorporated therein is anon-ionic surfactant, as novel compositions in their own right. These may be in a variety of forms and a preferred form, which is especially useful for the purposes of the analytical sensor devices and methods described herein, is that of a thin membrane. Their formation, the components from which they can be made, and the proportions of components are more fully described herein.

The sensor device may be applied to allow detection and measurement of electrolytically active species directly, i.e. when such species can pass through the membrane and then reach the active electrode (or any alternative detector which may be used in its place) and may be measured directly. However, we find that the invention is especially applicable to producing improved enzyme electrodes, in which an enzyme converts an analyte species into another species which is electrolytically active and can be detected at the active electrode, thereby providing an indirect measure of the analyte on which the enzyme acted.

Thus according to our invention we also provide, as a preferred embodiment, an improved sensor device which comprises (1) an active (working) electrode;

(2) an enzyme enclosed between two membranes - - -

(3) an inner membrane adjacent to the active electrode (1) and (4) an outer membrane positioned to contact a sample to be examined, characterised in that at least one of these two membranes comprises a modified polyurethane which is substantially non-porous and incorporates a non-ionic surfactant as modifier.

The mechanism by which our surfactant-modified polyurethanes function and are permeable is not yet clearly understood, but it is very surprising that these particular ones can be permeable towards a variety of low molecular weight species (e.g. sugars such as glucose) in solution—usually in aqueous solution—and do not necessarily have to be as small (in molecular terms) as gaseous materials.

The invention is not confined to use of an electrode as the means for detecting and measuring the analyte or another compound derived from it, i.e. electrochemical means, and any alternative detector may, if desired, replace the active electrode (1) specified in the sensor devices defined above. Likewise, although we find it most convenient to use amperometric measurement of electrochemical activity, and the invention is illustrated with particular reference to this mode, other modes of electrochemical measurement may be used if desired.

Preferably the surfactant-modified polyurethane is used to form the outer membrane (4), as this allows the benefits and advantages of the surfactant-modified polyurethane to be obtained. However, if desired, it may be used in a position which is not the outermost of the four parts specified above; for example, it may be desirable to add some further layer or screen over the modified polyurethane layer (4) to protect it from damage, or even, in some particular situation, to position the polyurethane layer between the active electrode and the enzyme layer, but the sequence set out above is the preferred one.

By the term "substantially non-porous" we mean that the surfactant-modified polyurethane it is not constructed or formed in a way that provides any discrete pores or holes in it, but nevertheless it is permeable.

The non-ionic surfactant may be any known surfactant compound. Especially it may be a compound having a molecular structure combining both (A) a hydrophilic moiety and (B) a hydrophobic moiety, in which the moieties (A) and (B) have sufficient activity for the combination to function as a surfactant.

Preferably, the non-ionic surfactant contains a poly-oxyalkylene chain, for example one derived from multiple units of poly-oxyethylene groups ($-CH_2-CH-O-$)$_n$. Such compounds are well known in the art and many are commercially available, usually being condensates of various proportions of ethylene oxide with a compound containing a hydrophobic moiety—especially with hydroxy-compounds, for example a phenol, a fatty alcohol, or the like, or mixtures thereof. A common one is a condensate of 7 to 10 molar proportions of ethylene oxide with an alkylated phenol, e.g. nonylphenol. Examples include condensates of ethylene oxide with sorbitan esters of higher fatty acids—e.g. sorbitan mono-laurate, mono-palmitate, mono-oleate or tri-oleate (for example those those available commercially under the name "Tween") and condensates of ethylene oxide with alkylated phenols or the like (for example those sold under the name "Triton"). The non-ionic surfactant may also contain other structures to impart the hydrophilic properties.

The non-ionic surfactant can be used to modify the polyurethane in various ways. Thus, a non-ionic surfactant may be incorporated into a polyurethane by simple admixture or thorough compounding to distribute it throughout the mass of the polyurethane. In this form, the non-ionic surfactant is trapped by the polyurethane and so is present within it, and is not present only as a surface coating. Methods for carrying out such admixture are well known in the art, as for example compounding techniques as are often used in the plastics industry for mixing the various ingredients of polymer compositions.

Alternatively, and preferably, the non-ionic surfactant may be incorporated into the polyurethane by allowing it to react chemically with the polyurethane so that it becomes chemically bound into its molecular structure. This may be done when the non-ionic surfactant contains a reactive substituent which can be reactive towards a reactive group in the polyisocyanate. Especially, one can use a surfactant containing a hydroxyl group and a form of polyisocyanate which still contains some free isocyanate groups; the hydroxyl and isocyanate groups are well know to be reactive towards each other and so can form the desired chemical bond—either of their own accord or under the influence of a catalyst and/or heat, as is conventional in the art of making polyurethanes. For this, a suitable polyurethane to use is one commonly know in the art as a "prepolymer"—i.e. a polyurethane made by interaction of polyurethane-forming ingredients using a stoicheiometric excess of the polyisocyanate component to provide the residual active isocyanate groups. Other polyurethane precursors, e.g. a polyisocyanate, may also be used as alternative (or in combination with) fully pre-formed polyurethanes, to provide some additional basis for the incorporation of the surfactant into the final polyurethane membrane.

The polyurethane may be any of those commercially available or known in the art, or combinations or mixtures thereof. The choice of the polyurethane and the non-ionic surfactant may be made on the basis of whether or not the surfactant is to be chemically bound as described above or not. They may also be chosen—and also the proportions of each—on the basis of the particular properties desired from each and for the resulting modified polyurethane.

It is important to recognise that, although many polyurethanes are made by reaction of a polyisocyanate with a polyol starting material which contains a chain of carbon atoms with interrupted at intervals by oxygen atoms (for example a polyethylene glycol, a polypropylene glycol and/or some similar compound)—so that the polyurethane contains polyethenoxy (or analogous) units—the presence of such units within the polyurethane structure is not sufficient to produce effects which are the purpose of this invention. We find it is necessary for any such polyethenoxy chains (or "blocks", as they are sometimes called) to be part of a surfactant component attached to or mixed with the conventional polyurethane.

The active (working) electrode (1) may be any of those known in the art or conventionally used, but is usually (and preferably) made of platinum metal. This may be associated, as in conventional practice, with such other features as one or more pseudo, counter or reference electrodes and the like.

The enzyme (2) enclosed between the two membranes (3) and (4) may be any of those known in the art, chosen to be an appropriate one which can act upon a selected substrate component in a sample to convert it into another species that can be detected at the active electrode.

Preferably, the enzyme is an oxidase—for example any of those which catalyse oxidation of lactate, pyruvate, oxalate, alcohol (ethanol) and the like, or a mixture or combination thereof. The one we find to be especially convenient and suitable for extensive commercial and clinical application is a glucose oxidase. An alternative enzyme may be a dehydrogenase.

According to our invention we also provide an improved method for analysis of samples characterised in that a sample containing a selected analyte is brought into contact with a sensor device as defined above.

The sensor device as a whole may be assembled in conventional manner, as the inventive feature is the nature of the modified polyurethane membrane used.

The sensor device may be made in a variety of forms, as may be considered most suitable or convenient for particular uses. Thus it may be in the form of a plate, probe or cell, which can be brought into contact with the fluid sample to be examined (or the sample may be brought into contact with it), for example by dipping, applying a sample dropwise, or by a flow of sample across the sensor device. These are usually conveniently suitable for in vitro use.

However, we prefer to make the sensor device in a needle form, so that it can more easily be placed into the sample to be examined; this is especially suitable for use of our sensor for in vivo measurements, as the needle can be of sufficiently small dimensions to be used with minimum difficulty, damage or inconvenience to the subject into which it is inserted.

An example of a way in which "needle" sensors can be made readily comprises taking a thin, PTFE-covered wire of the active electrode metal (e.g. platinum) and sealing this into a tube of a metal (e.g. stainless steel) which can act as a pseudo-reference electrode. Electrical contacts can be protected from access of the sample medium by enclosing the assembly in an enclosure (e.g. a syringe barrel housing) and sealing it at both ends, e.g. with an epoxy resin. PTFE from around the "advanced tip" working area is removed by scoring carefully with a blade, and the final construction may then be dip-coated with successive membrane layers. Applying the coating as the final step in basic electrode fabrication minimises the risk of possible membrane damage.

The composition and thickness of the modified polyurethane membrane may be varied according to the particular requirements desired for the performance of the sensor device and the system and analyte to be analysed. The main requirement is that it should be thick enough to be durable in use and not too fragile, but thin enough to have the desired degree of permeability to let the relevant components pass through.

Typically, the polyurethane membrane thickness may be up to 10 microns ($\mu$m) and preferably in the range 0.01 to 1.0 microns ($\mu$m), though it may be greater or less than this if desired.

The membrane which is not a polyurethane (when this is used, as in the preferred embodiments of this invention) may be any of those known in the art as appropriate for use as membranes in sensors and having sufficient permeability to allow any relevant component to pass through it—for example from the sample under examination or, especially, to allow an electroactive product formed by interaction of the enzyme layer with an analyte (which has passed through an outer polyurethane membrane from the sample under examination) to reach the active electrode and be detected there.

This "non-polyurethane" membrane may be made of any material and may be in any of the forms known in the art to be appropriate for use as a membrane in a sensor device. Such a membrane may have a thickness in the range 0.01 to 10 microns ($\mu$m), and preferably in the range 0.01 to 1.0 microns ($\mu$m), but thicker or thinner ones may be used if desired.

Examples of materials which may be used to make the "non-polyurethane" membrane include cellulosic materials, e.g. cellulose acetate; polycarbonates; polysulphones and polyethersulphones, especially sulphonated and un-sulphonated polyaryl sulphones (sometimes referred to as "SPEES-PES" polymers) and sulphonated and un-sulphonated polyaryl ketones (which are more fully described in European Patent No. 225094) and mixtures or combinations thereof. These may be of porous or non-porous form to whatever extent is found satisfactory to allow the desired permeability.

When an oxidase enzyme is used, its effect is to form hydrogen peroxide, which can permeate readily through a variety of materials (porous or not); this allows a wide choice for the material and form to use as the inner membrane.

The various membranes (especially the modified polyurethane, but also others) may be made by conventional methods, for example by rolling, cutting from a mass, casting from solution, or combinations of such techniques, optionally with inclusion of additives (for example by inclusion in the casting solution) to modify the properties of the resulting cast film or to facilitate the casting process. Our preferred methods for the modified polyurethane are those based on deposition from solution, for example by dipping ("dip-coating"), spraying, painting or the like; the deposition step (e.g. dip-coating) may be repeated as many times as may be desired to build up any required total thickness or to vary the composition of the successive deposits to secure a variation of composition through the layer. The thickness of any deposited layer thus formed may be varied according to the viscosity and other properties of the solution and its components.

In general, the optimum thickness and composition of any membrane for any particular case can be found by simple trial.

The proportion of the non-ionic surfactant to be used in the polyurethane may vary over a considerable range. The optimum will depend very much on the particular used and conditions in which the sensor device is employed, and may be found by simple trial. In general, we prefer to use the surfactant is used in a proportion, relative to the polyurethane, greater than would be required merely to assist in wetting the membrane or making a dispersion of the polymer from which it is made. Conveniently, the proportion may be in the range from 3 to 20 parts (by volume) of the non-ionic surfactant per 100 parts (by volume) of the polyurethane, but larger or smaller proportions may be used if desired. The proportion of surfactant may be made approximately uniform throughout the polyurethane membrane or it may vary, so providing a "concentration gradient" of the surfactant content through the membrane.

Sensors according to the present invention enable the reliable measurement or detection ranges for glucose in many media, including biological media, and are especially useful for taking measurements if biological media in vivo. For this, the sensor devices of the present invention allow implanted electrodes to provide a satisfactorily steady output signal within a reasonable time after implantation, and also detect dynamic fluctuations in glucose content. This makes the sensors much more useful in practical clinical or laboratory conditions than those previously known, as well as being useful for in vitro measurement—e.g. of fruit, meat, animal products and the like.

In use, the electrode of our invention can be used to carry out the method of our invention by simple immersion in a predetermined volume of a buffered solution to be analysed, and applying a voltage so that amperometric measurements can be made. If desired, the procedure may also be calibrated by use of solutions containing known amounts of the analyte (e.g. glucose) sought, and its accuracy thus checked and confirmed. Likewise, the procedure may be carried out using known amounts of compounds which are considered to be potentially troublesome by their expected ability to interfere with the measurement, so that the degree of interference (if any) can be established. Conventional apparatus may be used for the cell, electrodes and carrying out the measurement and recording of the amperometric relationships for the samples under test. Measurements may be made continuously or intermittently, as desired.

Conventional apparatus may be used, for the cell, electrodes and for measurement and recording of the current-voltage relationships for the samples under test. Measurements may be made continuously or intermittently, as desired, and recorded for reference or assessment.

In operating the procedure amperometrically, it is convenient to use a polarising voltage in the conventional range +0.4 to +0.8 volts (and preferably at approximately +0.650 volt) against a silver/silver chloride electrode, but other voltages may be used if so desired. The liquid sample being examined may be at a pH which can vary over a considerable range, but is especially in the range pH 6 to pH 8 and preferably at approximately pH 7.4 (for physiological use).

A fluid (liquid) sample under examination may be stirred or unstirred, as desired or convenient.

The electrolytic procedure for use of the sensors of our invention may be carried out over a considerable range of temperatures, for example in the range 20 to 40 degrees C., but higher or lower temperatures may be used if desired. Operation at lower temperatures, around or even below zero degrees C., enables the sensor devices of our invention to be used for testing in cold storage conditions. It is usually preferred that any calibration is carried out at a temperature within approximately 4 degrees C. of temperature at which the sensor is to be used.

The medium comprising the sample examined is commonly aqueous, but need not necessarily be so, and one or more organic solvents may be used if desired (as such, or in admixture with each other and/or water) provided the medium is an electrolyte and dissolves any desired reagents, but does not attack any of the sensor components, e.g. enzyme and/or a membrane. It is preferred that the sample and any other media used should not leach out the surfactant too readily. In general, the incorporation of surfactant into the polyurethane is sufficient to avoid any problems in this respect, and aiming for reaction between the surfactant and the polyisocyanate helps to stop such leaching.

For use in vitro, the sensor may be immersed in a sample of the liquid under examination or the sample may be applied to it (for example by droplets).

The electrode of the sensor device is linked with any conveniently suitable system for measuring the current flow when a potential is applied to the electrode (amperometric measurement). This may be done in conventional manner, using conventional equipment. Measurements of the impedance (resistance) may be taken and the measurements taken and recorded as desired, intermittently or continuously. For this, conventional apparatus may be used.

Samples of the media for examination may be obtained by standard methods, and the quantity of sample should be sufficient to cover the sensor and the current measured at a fixed time or after a stable response has been achieved. Likewise, samples of other media may be obtained in any convenient manner and brought into contact with the sensor of the present invention for the purpose of component detection.

An especially useful feature of the surfactant-modified polyurethanes have a very good bio-compatibility, together with an excellent resistance to fouling, which makes them very suitable for use in clinical sensor devices. Further, our sensor devices have the unusually advantageous property of being able to provide a good and reliable measure of the content of analytes in biological media—and this extends to measurements in tissue as well as in free blood, with excellent correlation between these two for a given subject. This means that the previous emphasis in practice on sampling biological fluids (e.g. whole blood) are no longer essential as adequately reliable results can be obtained by mere insertion of the sensor (especially if constructed in a "needle" form) into the tissue. Also, we have found that the in vitro sensitivity of our sensor devices after use by implantation in an in vivo system has not varied—which means that, in addition to no fouling of the sensor, there is no need for the sensor to be calibrated again in vivo. Also, the contact between sensor and tissue appears improved to the extent that it can show performance of the level expected when using micro-flow (feeding liquid to the sensor/tissue interface) and not obtained with conventional polyurethanes. The reason for this is not understood, but it may be due to a change in the sensor-liquid/tissue contact and is important. The conditioning time can also be reduced.

The invention is illustrated but not limited by the following Examples and accompanying drawings.

EXAMPLE 1

The construction of a sensor electrode can be seen by reference to the accompanying drawings which are only schematic and not drawn to scale.

Figure 2:
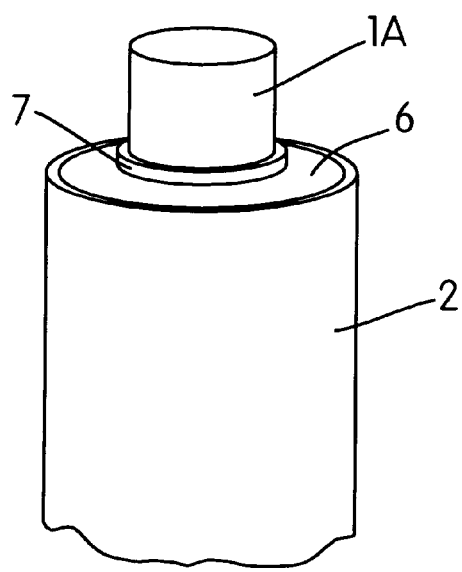

FIG. 1 represents a view of a sensor device according to our invention, shown in cross-section, and FIG. 2 shows it in a perspective view, prior to application of membranes. A length of thin platinum wire (1) covered with an insulating coating of PTFE (polytetrafluoroethylene) (7) is sealed into a stainless steel tube (2) by being inset into it with a filling of an epoxy resin (6) which holds the coated platinum wire securely within the stainless steel tube and gives the desired sealing and insulating effect.

The tip section (1A) of the coated platinum wire, which protrudes from the embedding epoxy resin (6) is carefully scored with a blade to strip off the PTFE coating and expose the bare platinum metal. This exposed platinum wire is to serve as an "active" electrode and the stainless steel tube as a pseudo reference electrode.

The exposed platinum wire tip (1A) is then completely covered by a layer (3) of a permselective sulphonated polyarylethersulphone (SPEES) polymer. This polymer layer (3) extends over the whole of exposed surface of the platinum wire (1A) and overlaps on to the surface of the surrounding stainless steel tube (2).

In turn, the polymer layer (3) is covered with an enzyme layer (4) of glucose oxidase immobilised thereon.

The enzyme layer (4) is then covered completely with a layer (5) of a surfactant-modified polyurethane which serves as a outer membrane which also extends to cover the surrounding support base (1), so ensuring a liquid-tight seal which prevents any applied sample liquid by-passing the enzyme and polymer layers to reach the platinum electrode directly.

Suitable provision is made (not shown) for the platinum electrode (1) and the stainless steel tube (2) to be connected electrically to external measuring circuits.

The permselective layer (3) comprising the sulphonated polyaryl-ethersulphone (SPEES) polymer is made by deposition from a 10% (w/v) solution of the polymer in dimethyl sulphoxide.

The immobilised enzyme layer (4) is formed by depositing a solution comprising 30 mg/ml of glucose oxidase (activity 180 U/mg), 200 mg/ml bovine serum albumin and 10 mg/ml sodium heparin dissolved in phosphate buffered saline (adjusted to pH 7.4) and thoroughly dissolved. This solution (6 ul) is mixed with a 5% (v/v) solution of glutaraldehyde in phosphate buffered saline (3 ul) to cross-link the enzyme, and a drop of the mixed solution is dip-coated over the inner membrane (3) for approximately 2 seconds at ambient temperature and then dried for 30 minutes. The coated electrode tip is then washed for 15 minutes in phosphate buffer and dried overnight.

The coating with surfactant-modified polyurethane is made by holding the enzyme-coated wire electrode in a vertical position and treated to form an outer membrane of modified polyurethane by dipping into a solution comprising 2% (v/v) of Triton X100 (the surfactant component) and 10% (v/v) of Trixene SC762 (the polyurethane component) dissolved in tetrahydrofuran (THF). The dipping (dip-coating) of the electrode was for a few seconds at a time followed by raising it from the solution and draining and air-drying it. This dipping procedure was repeated at 30-minute intervals using solutions containing successively greater proportions of the Trixene SC762—16%, then 33% and finally 50% of Trixene SC762, each with 2% of the Triton X100—and then air-dried at ambient temperature overnight. The resulting layer (5) of a surfactant-modified polyurethane is thus a composite one made up of four successive layers in which the proportion of surfactant decreases towards the outer face.

A sensor device, constructed as described above, was made using a piece of platinum wire 0.125 mm outside diameter and allowing about 0.25 mm of its length to protrude and act as a platinum anode working electrode. The size of the stainless steel tube is not critical, and was approximately 0.5 mm outside diameter. (A smaller stainless steel tube can be used for a finer platinum wire—for example 0.25 mm outside diameter for a platinum wire 0.05 mm diameter.)

Then, the resulting multi-coated electrode was immersed in YSB buffer solution (Yellow Springs Buffer solution, a phosphate-buffered saline solution of pH 7.4) for 3 to 24 hours to condition it, and then calibrated in buffer solutions at 37 degrees C. containing various amounts of glucose up to 30 mM. The calibration showed a linearity exceeding 20 mM, response time ($T_{90}$) less than 2–3 minutes and sensitivity 0.1–0.9 nA/mM. Electrodes were also calibrated in whole blood and showed no drift in sensor responses and and post-blood re-calibration in buffer showed fouling to be nil or negligible.

In vivo monitoring was carried out using coated electrodes (conveniently referred to as "needle" electrodes) made as described above, pre-calibrated and conditioned in buffer solution. The electrode was implanted in subcutaneous tissue of anaesthetised male Sprague-Dawley rats (using sodium pentobarbitone, 60 mg/kg body mass), and the implanted electrode was connected to a conventional system for amperometric analysis.

The implanted electrodes achieved a steady current within 30 to 60 minutes and dynamic fluctuations in the tissue glucose levels were detected consistently within 1 to 3 minutes following intravenous glucose injection and within 3 to 7 minutes following insulin administration.

The determination of subcutaneous tissue glucose showed a reliable correlation with blood glucose levels measured using a standard clinical technique (Yellow Springs Analyser), yielding an $r^2$ value of 0.97 for a study of five electrodes. Post-implantation calibration study (less than 4 hours later) showed the changes in electrode sensitivity to be nil or negligible.

This shows that the coated electrodes described above show an excellent performance, even the more demanding conditions of in vivo use.

"Trixene SC762" is a polyurethane solution commercially available from Baxenden Speciality Chemicals Division, Accrington, Lancashire BB5 2SL, England, and described by them as "an isocyanate prepolymer in solution" with terminal isocyanate groups, dissolved in toluene, ethyl acetate, and methyl isobutyl ketone.

"Triton X100" is a commercially available condensate of 4-octylphenol with approximately 10 molecular proportions of ethylene oxide, in which the octyl substituent is stated in supplier's list as 1,1,3,3-tetramethylbutyl.

What is claimed is:

1. Sensor device which comprises a detector means and a membrane positioned to protect the detector from direct contact with a sample to be examined, characterised in that the said membrane comprises a modified polyurethane which is substantially no-porous and incorporates an non-ionic surfactant as modifier.

2. Sensor device as claimed in claim 1 wherein the detector means is an active (working) electrode.

3. Sensor device as claimed in claim 2 wherein the active (working) electrode is an enzyme electrode, in which an enzyme converts an analyte species into another species which is electrolytically active and can be detected at the active electrode, thereby providing an indirect measure of the analyte on which the enzyme acted.

4. Sensor device as claimed in claim 3 which comprises
   (1) an active (working) electrode,
   (2) an enzyme enclosed between two membranes,
   (3) an inner membrane adjacent to active electrode (1) and
   (4) an outer membrane positioned to contact a sample to be examined, characterised in that at least one of these two membranes comprises a modified polyurethane which is substantially non-porous and incorporates a non-ionic surfactant as modifier.

5. Sensor device as claimed in any of claims 1 to 4 wherein an electrolytically active analyte species is detected directly, i.e. when such species can pass through the membrane and then reach the active electrode (or any alternative detector which may be used in its place) and may be measured directly.

6. Sensor device as claimed in any of claims 1 to 5 wherein the non-ionic surfactant is a compound having a molecular structure combining both (A) a hydrophilic moiety and (B) a hydrophobic moiety, in which the moieties (A) and (B) have sufficient activity for the combination to function as a surfactant.

7. Sensor device as claimed in any of claims 1 to 6 wherein the non-ionic surfactant contains a poly-oxyalkylene chain, for example derived from multiple units of poly-oxyethylene groups ($—CH_2—CH—O—)_n$, preferably a condensate of ethylene oxide with a compound containing a hydrophobic moiety—especially with a hydroxy-compound.

8. Sensor device as claimed in any of claims 1 to 7 wherein the non-ionic surfactant is derived from a phenol, alkylated phenol, fatty alcohol, sorbitan ester of a higher fatty acid, or a mixture thereof.

9. Sensor device as claimed in any of claims 1 to 8 wherein the non-ionic surfactant is incorporated into a polyurethane by simple admixture or thorough compounding to distribute it throughout the mass of the polyurethane.

10. Sensor device as claimed in any of claims 1 to 9 wherein the non-ionic surfactant is incorporated into the polyurethane by allowing it to react chemically with the polyurethane so that it becomes chemically bound into its molecular structure.

11. Sensor device as claimed in any of claims 1 to 10 wherein the non-ionic surfactant contains a substituent which can be reactive towards a reactive group in the polyisocyanate, especially by using a surfactant containing a hydroxyl group and a form of polyisocyanate which still contains some free isocyante groups, whereby the hydroxyl and isocyanate groups are well known to be reactive towards each other and so can form the desired chemical bond.

12. Sensor device as claimed in any of claims 1 to 11 wherein the active (working) electrode is made of platinum metal, optionally associated with one or more pseudo, counter or reference electrodes.

13. Sensor device as claimed in any of claims 1 to 12 wherein the enzyme is an oxidase—for example any of those which catalyse oxidation of lactate, pyruvate, oxalate, glucose, alcohol (ethanol) or a dehydrogenase.

14. Sensor device as claimed in any of claims 1 to 13 which is made in a needle form.

15. Sensor device as claimed in any of claims 1 to 14 wherein the thickness of the polyurethane membrane is up to 10 microns (μm) and preferably in the range 0.01 to 1.0 microns (μm).

16. Sensor device as claimed in any of claims 1 to 15 wherein the proportion of the non-ionic surfactant to be used in the polyurethane in the range from 3 to 20 parts (by volume) of the non-ionic surfactant per 100 parts (by volume) of the polyurethane.

17. Sensor device incorporating a membrane made of a surfactant-modified polyurethane, substantially as described.

18. Method for analysis of samples characterised in that a sample containing a selected analyte is brought into contact with a sensor device as claimed in any of claims 2 to 17.

19. Method as claimed in claim 18 wherein a sensor device as claimed in any of claims 1 to 17 is immersed in a predetermined volume of a buffered solution to be analysed.

20. Method as claimed in claim 18 or claim 19 wherein the detector is an electrode and measurements are made by applying a voltage to the electrode so that amperometric measurements can be made.

21. Method for analysis of samples using a sensor device substantially as described.

22. Method for making a sensor device as claimed in any of claims 1 to 17 which comprises applying the membrane layers, especially the modified polyurethane layer, from a solution of the membrane material by dip-coating.

* * * * *